United States Patent [19]
Shimada et al.

[11] Patent Number: 4,564,012
[45] Date of Patent: Jan. 14, 1986

[54] LASER SURGICAL EQUIPMENT

[75] Inventors: Tamotsu Shimada, Akishima; Chiaki Shinbo, Mitaka; Hideyuki Horiuchi, Kokubunji; Masamoto Takatsuji, Setagaya, all of Japan

[73] Assignee: Hitachi, Ltd., Tokyo, Japan

[21] Appl. No.: 421,402

[22] Filed: Sep. 22, 1982

[30] Foreign Application Priority Data
  Sep. 28, 1981 [JP] Japan ............... 56-152083
  Sep. 28, 1981 [JP] Japan ............... 56-152084

[51] Int. Cl.[4] ........................... A61N 5/06
[52] U.S. Cl. ................... 128/303.1; 128/395; 219/121 LB
[58] Field of Search ...... 128/303.1, 395, 6, 396–398; 219/121 LB, 121 L, 121 LA, 121 LF, 121 ET, 121 EG; 250/252.1, 264–265

[56] References Cited
U.S. PATENT DOCUMENTS
3,703,176 11/1972 Vissiliadis et al. ........... 128/395
4,316,467 2/1982 Mulkerheide ............... 128/303.1
4,378,492 3/1983 Nagashima et al. .......... 250/215

FOREIGN PATENT DOCUMENTS
2832847 2/1980 Fed. Rep. of Germany ... 128/303.1
1579601 11/1980 United Kingdom ......... 219/121 LB

*Primary Examiner*—Lee S. Cohen
*Assistant Examiner*—Steven Falk
*Attorney, Agent, or Firm*—Antonelli, Terry & Wands

[57] ABSTRACT

In a laser surgical equipment consisting of a laser oscillator oscillating a laser output, an optical waveguide connected to the laser oscillator and transmitting the laser output and a hand piece connected to the optical waveguide and radiating the laser output to a diseased part to be radiated, the improvement comprising a detector for detecting the laser output from the hand piece, a comparator for comparing the output of the detector with a predetermined value and a controller for controlling the laser oscillator by the output of the comparator and for setting the laser output of the hand piece to the predetermined value.

15 Claims, 18 Drawing Figures

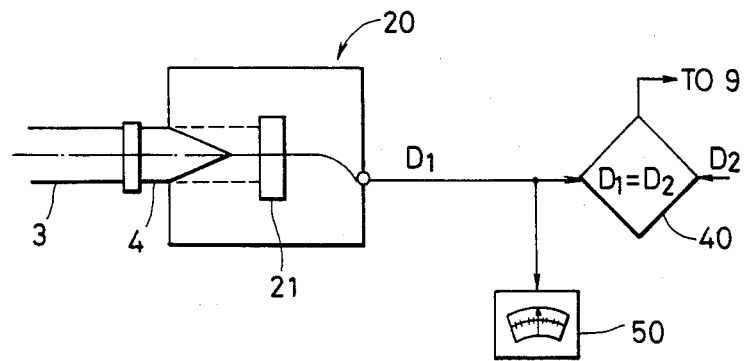
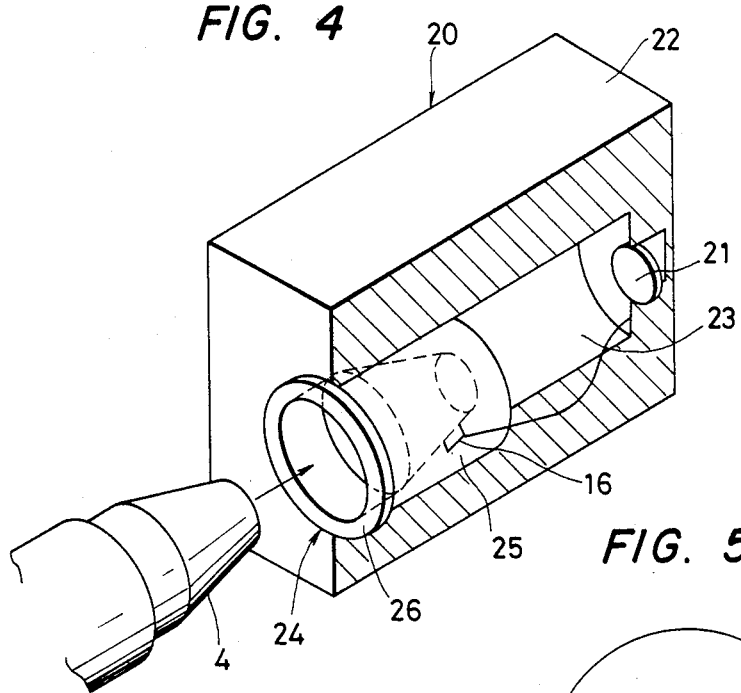
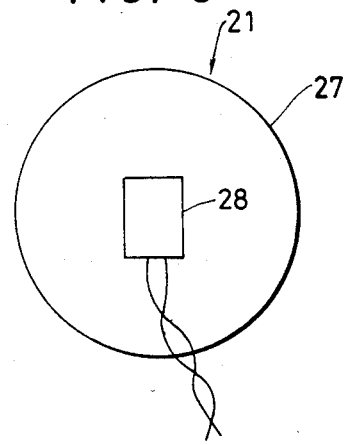

LASER SURGICAL EQUIPMENT

BACKGROUND OF THE INVENTION

This invention relates to a laser surgical equipment and more particularly, to a laser surgical equipment for surgical operation.

Steel knives have been used in the past for surgical operation in hospitals but so-called laser surgical equipments using laser light have been used in recent years. FIG. 1 shows diagrammatically the construction of a typical conventional laser surgical equipment. The laser light is generated by a laser oscillator 2 such as a carbon dioxide ($CO_2$) laser disposed inside a laser oscillation apparatus 1 and is transmitted to a desired position while being guided by a waveguide 3 such as a multi-joint reflection mirror type manipulator or an optical fiber guide. The laser light is then condensed by a hand piece 4 fitted to the tip of the waveguide 3 and is radiated to a diseased part 5 for cutting, coagulation of blood, and so forth.

During the surgical operation, the operator must frequently adjust the laser output to be emitted from the hand piece depending upon the diseased parts. For example, suitable laser output is about 20 W for skin incision, about 30 W for excision of tumor and about 50 W for amputation of bone. In the conventional laser surgical equipment, the output control of the laser light obtained from the laser oscillator 2 is effected by operating a manual control device 8 disposed on a control panel 7 of a laser oscillation control apparatus 6 and by controlling the oscillation current by a laser controller 9 disposed inside the laser oscillation control apparatus. In this case, a power meter 13 consisting of a beam splitter 11 and a photo-detector 12 for detecting the reflected light from the beam splitter 11, for example, is disposed inside the optical path in the vicinity of the emitting portion of the laser oscillator 2 in order to detect the laser output and the output of the detector 12 is fed to a laser power indicator 10 to check the laser power. In accordance with this detection method, however, the laser power at the diseased part 5 can not be detected. In other words, there occurs the problem that changes of the laser power arising from deviation of the optical axis of the waveguide 3, fatigue of the reflecting mirror, fatigue of condenser lenses incorporated in the hand piece 4 and so forth can not be corrected. This problem results in the drop of so-called "beam depth (sharpness)" and critically affects the life itself of a patient because coagulation of blood at the bleeding part becomes impossible due to the shortage of the laser power, for example.

In the conventional laser surgical equipment, further, if the laser output at the tip of the hand piece drops, it is not possible to correctly determine at which portion or portions of the laser oscillator, waveguide and hand piece the problem occurs. This is the fatal problem for medical equipment in general which must always operate stably.

SUMMARY OF THE INVENTION

In view of the problems described above, the present invention is directed to provide a laser surgical equipment which can accurately measure the laser power at the diseased part and can automatically set the laser power to a necessary level and which has high reliability.

It is another object of the present invention to provide a laser surgical equipment which can accurately detect the portion of trouble and which has improved reliability.

To accomplish these objects, the laser surgical equipment in accordance with the present invention is characterized by including photoelectric conversion means for receiving the laser light from the hand piece and converting it into an electric signal and an automatic laser power adjuster for controlling the laser power intensity so as to adjust the output signal from the photoelectric conversion means to a desired value.

Furthermore, the laser surgical equipment of the present invention is characterized by including a self-diagnostic system which makes it possible to detect abnormality of each element of the laser surgical equipment.

BRIEF DESCRIPTION OF THE DRAWINGS

FIG. 3 is a schematic view of the laser power meter to be used in the present invention;

FIG. 4 is a sectional view showing in detail the laser power meter;

FIG. 5 is a schematic view of the detector to be used in the present invention;

DESCRIPTION OF THE PREFERRED EMBODIMENTS

Figure 1:
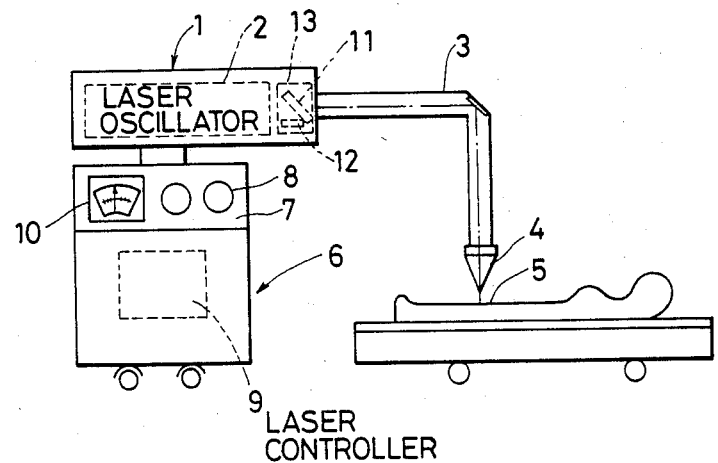
FIG. 1 is a schematic view of the conventional laser surgical equipment.
Figure 2:
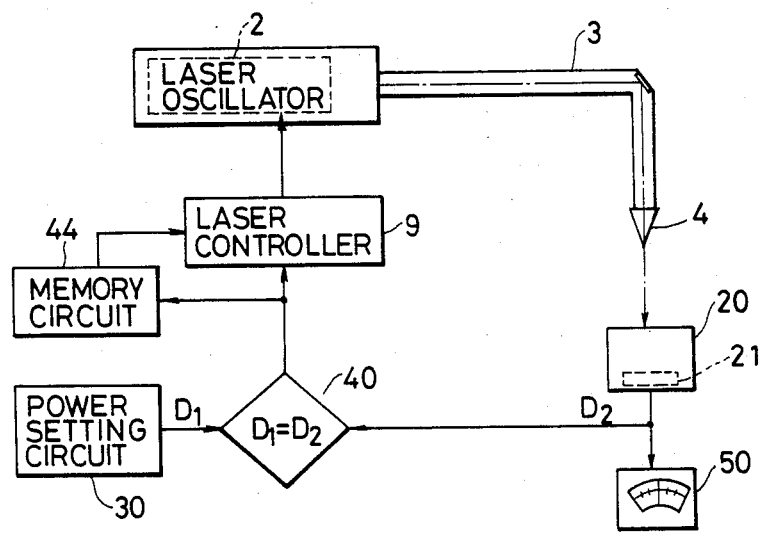
FIG. 2 is a block diagram of the laser surgical equipment in accordance with one embodiment of the present invention.

FIG. 2 is a block diagram showing diagrammatically the construction of the laser surgical equipment in accordance with one embodiment of the present invention. In the drawing, the laser oscillator 2, the waveguide 3, the hand piece 4 and the laser power controller 9 have the heretofore known construction. In other words, the laser light generated from the laser oscillator 2 such as a $CO_2$ gas laser generator is transmitted to a desired position while being guided by the waveguide 3 such as a multi-joint reflecting mirror type manipulater or an optical fiber, is condensed by the hand piece 4 and is then emitted from the tip of the hand piece 4. The laser power is controlled as the power controller 9 including a power source changes the oscillation current of the laser oscillator 2.

The laser surgical equipment in accordance with the present invention is characterized by including an automatic laser power adjuster which consists of a laser power meter 20 equipped with a photo-detector 21 for detecting the output of the laser light emitted from the tip of the hand piece 4; a power setting circuit 30 for setting the laser power to a desired power intensity; a comparison circuit 40 for comparing the output $D_2$ of the photo-detector 21 with the output $D_1$ of the laser power setting circuit 30 and controlling the laser controller 9 so that both outputs $D_1$ and $D_2$ become equal to each other; and a memory circuit 44 for storing the output corresponding to the result of comparison of the comparison circuit.

The automatic laser power adjustment in accordance with the present invention is effected before the operator starts the surgical operation and corresponds to the starting check of the surgical equipment. The operation is initiated by first inserting the hand piece 4 into the laser power meter 20. The photo-detector 21 receives the laser light emitted from the hand piece 4 and the light is converted to the electric output $D_2$. This output $D_2$ is applied to the comparison circuit 40. On the other hand, the output $D_1$, which corresponds to the intensity of the laser light which is set by the laser power setting circuit 30 and is to be secured, is also applied to the comparison circuit 40. The comparison circuit 40 compares this output $D_1$ with the output $D_2$ of the photo-detector 21 and controls the output current of the laser power controller 9 so that both outputs coincide with each other and the laser power of the laser oscillator 2 can thus be controlled. If the output $D_2$ is smaller than the output $D_1$, for example, the output of the comparison circuit 40 increases and the driving current of the laser oscillator increases until the output $D_2$ becomes equal to $D_1$. In this manner, the laser power from the hand piece 4 remains stable at the intensity which is set by the laser power setting circuit 30. In this case, a power indicator 50 is disposed and if the output of the photo-detector 21 is applied to the indicator 50, the laser power from the hand piece can be checked more conveniently.

There exists the disadvantage that the laser power from the hand piece changes due to deviation of the optical axis of the waveguide 3, deviation of the reflecting mirror and degradation of the condenser lenses incorporated in the hand piece. However, the output at the tip of the hand piece can be obtained accurately and automatically in accordance with the construction described above even if fatigue of the waveguide and that of the optical system of the hand piece and deviation of the optical axis occur. Hence, the surgical operation can be carried out with a stable beam depth.

FIG. 3 illustrates the laser power meter 20 to be used in the present invention. In the drawing, the hand piece 4 is shown inserted into the laser power meter 20. When the laser light is emitted under this state through the waveguide 3 and the hand piece 4, the energy of the laser light is detected by the photodetector 21 and its output is applied to the comparison circuit 40.

If the power indicator 50 is provided, the output of the photo-detector 21 is also applied to the power indicator and the output value can be displayed as shown in FIG. 3.

The construction of the laser power meter 20 will be described in further detail with reference to FIG. 4.

FIG. 4 is a sectional view of the laser power meter. The drawing shows the state immediately before the hand piece 4 is inserted into the laser power meter 20. In this example, the laser power meter 20 consists of a support member 24 for supporting the hand piece 4, a case 22 for supporting the support member 24 and a photo-detector 21 for receiving the laser light emitted from the hand piece 4. This arrangement makes it possible to use the laser power meter 20 as the support means for the hand piece and is extremely effective. The support member 24 consists of a cylindrical portion 25 having an inner wall having substantially the same profile as the outer profile of the hand piece and a ring-like tongue 26 disposed at one end of the cylindrical portion. In order to reliably support the hand piece 4 without damaging it, the support member 24 is preferably made of a flexible material such as rigid rubber or its inner wall, which comes into contact with the hand piece, is preferably coated with such a flexible material. The case 22 consists of a rectangular member and a columnar hole 23 which has a diameter which is substantially equal to the outer diameter of the cylindrical portion 25 of the support member 24 and which is sufficiently deeper than the length of the cylindrical portion 25 is bored at the center of the rectangular member. The cylindrical portion 25 of the support member 24 is fitted into this hole 23 and is held in place. The depth of the hole is preferably set in such a manner that when the hand piece 4 is fitted into the support member 24, the bottom surface of the hole 23 is positioned close to the focal point of the laser light emitted from the hand piece. The photodetector 21 is placed on the bottom surface of the hole 23 so as to receive the laser light from the hand piece. Needless to say, the hole 23 may have substantially the same shape as the outer shape of the hand piece 4 so that the case 22 has the function of the support member 24. Furthermore, a proximity switch 16 is disposed so as to automatically detect the state in which the hand piece 4 is fitted into the laser power meter 20. The proximity switch may be of such a type which detects the change of electrostatic capacitance when the hand piece comes into contact with it, for example.

An example of the photo-detector 21 is shown in FIG. 5. The drawing illustrates the case when the photo-detector is viewed from the side opposite the light receiving plane and the laser light is incident from the reverse of the drawing. The energy of the laser light is absorbed by a metallic plate 27 such as an aluminum plate whose surface (light receiving surface) is coated in black, for instance. A thermoplie 28 such as a multi-element bismuth-antimony thermopile converts the temperature rise of the metallic plate 27 upon absorption of the energy into the thermoelectromotive force and thus detects the energy of the laser beam.

Figure 6:
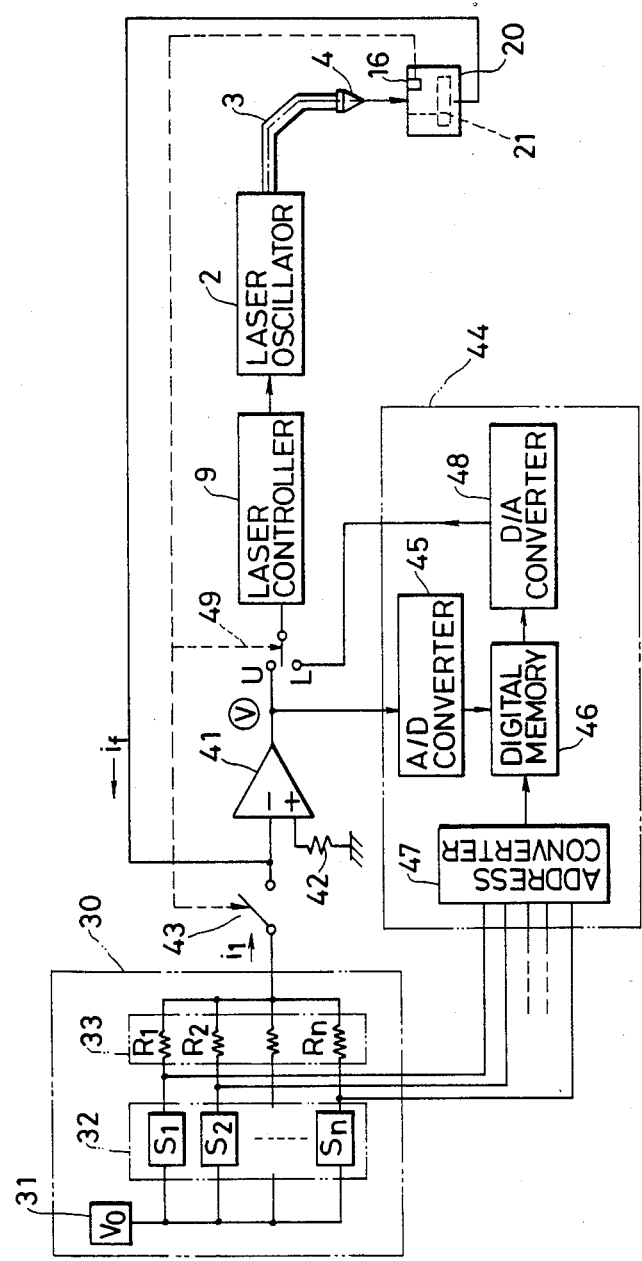
FIG. 6 is a block diagram of the automatic laser power adjuster in accordance with the present invention.

Next, the laser power setting circuit 30 will be described. FIG. 6 shows an example of the automatic laser power adjuster in accordance with the present invention together with an example of the laser power setting circuit 30. The laser power setting circuit 30 consists of a voltage source 31, a switch group 32 and a resistor group 33. The switch group 32 consists of a plurality of switches $S_1, S_2, \ldots, S_n$ one end each of which is connected to the voltage source and the resistor group 33 consists of a plurality of resistors $R_1, R_2, \ldots, R_n$. One end each of the resistors is connected to the other end each of the switches while the other end each is connected in common to the negative terminal of an operational amplifier 41. The output of the laser power meter 20 is also applied to the negative terminal of the operational amplifier 41 and its positive terminal is grounded via a resistor 42. This amplifier 41 forms the comparison circuit 40.

When the hand piece 4 is inserted into the laser power meter 20, the proximity switch 16 operates, the switch 43 is turned on and the switch 49 automatically selects the terminal U. If the switch $S_1$ is turned on, for example, the resistor $R_1$ is selected and a current $i_1$ is applied to the operational amplifier 41. In this case, since the laser light is not yet applied to the photo-detector 21 of the laser power meter 20, another input current $i_f$ to the operational amplifier 41 is "0". Hence, a voltage corresponding to the current $i_1$ is generated at the output of the operational amplifier 41 and is applied to the laser power controller 9. The laser controller 9 generates the oscillation current of the laser oscillator 2 in accordance with this voltage and controls the laser power. The photo-detector 21 receives the laser light and converts it to the current $i_f$. This output current $i_f$ is fed back to the operational amplifier 41, which compares the two input currents $i_1$ and $i_f$ with each other and controls the laser controller 9 until the difference of the two currents becomes zero (0). In this manner, the laser light from the hand piece remains stable at the output level that is set by the switch $S_1$.

The voltage value of the voltage source 31 and the values of the resistors $R_1, R_2, \ldots, R_n$ of the resistor group 33 shown in FIG. 6 may be set in the following manner. If the laser power set by the switch $S_1$ is 10 W, for example, the voltage value $V_o$ and the resistance of the resistor $R_1$ are decided so that the current $i_1$ which flows when the switch $S_1$ is selected becomes equal to the output current $i_f$ obtained from the photo-detector 21 for the 10 W laser light. It will be assumed that the output current $i_f$ of the photo-detector 21 is 10 mA when the laser power is to be set to 10 W by the switch $S_1$. In this case, the values of the voltage of the voltage source 31 and the resistor $R_1$ may be set to 5 V and 500 Ohms, respectively. The other resistors can also be set in the same way. When the laser power is set to 20 W by the switch $S_2$, the resistor $R_2$ may be set to 250 Ohms because the output current $i_f$ of the photo-detector becomes 20 mA substantially proportionally to the laser power.

The photo-detector 21 of the embodiment shown in FIG. 6 can not be used during the surgical operation. Accordingly, the memory circuit 44 is connected to the output of the operational amplifier 41 in order to store the result obtained by the automatic power adjustment described above. The memory circuit can store the voltage V when the current $i_1$ of the power setting circuit becomes equal to the output current $i_f$ of the photo-detecter 21. The memory circuit 44 consists of an A/D converter 45, a digital memory 46, an address converter 47 and a D/A converter 48. The output voltage V of the operational amplifier 41 is converted to a digital quantity by the A/D converter 45 and is stored in the memory 46. When the hand piece 4 is not fitted into the laser output meter 20 and the laser light is not received by the photo-detector 21 (or during the surgical operation), the switch 43 is kept OFF by the signal from the proximity relay 16 and the switch 49 automatically selects the terminal L. Thus, the operational amplifier 41 is cut off from the circuit during the surgical operation and the laser power is decided by the memory circuit 44. In other words, the address convertor 47 reads the data of the memory 46 in response to the power setting switches $S_1$ through $S_n$. The D/A converter 48 converts the data to the analog quantity and applies it to the laser controller 9. If the output voltage of the operational amplifier 41 is V when the switch $S_1$ is selected, for example, it is obvious that the voltage V is applied to the laser oscillator 9 even during the surgical operation.

Figure 7:
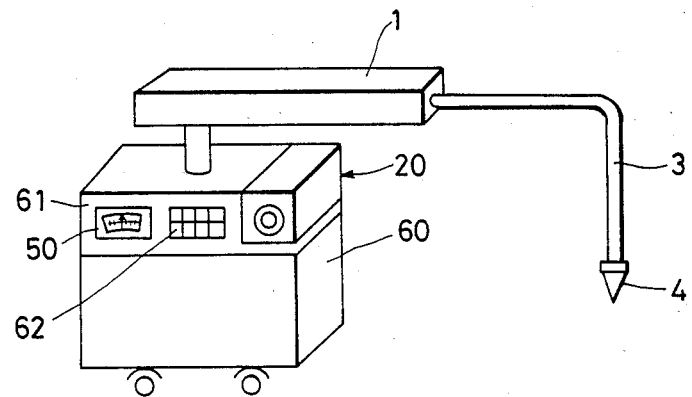
FIGS. 7 and 8 are perspective views of the laser surgical equipment in accordance with the present invention.

FIG. 7 shows the appearance of the laser surgical equipment in accordance with the present invention. In the drawing, reference numeral 60 represents the case of the laser oscillation controller, and the laser power controller 9 and the like are disposed in this case. Reference numeral 61 represents a control panel placed on the case 60. The laser power setting circuit 30, the comparison circuit 40 and like are disposed inside the control panel. The indicator 50 and a push switch group 62 including the switch group 32 of the laser power setting circuit 30 are disposed on the panel surface of the control panel. Besides the push switches, the switch group 32 may use slide volume switches or rotary switches that select the resistance either continuously or stepwise so as to set the laser power. A mechanical indicator of a point type and electronic displays such as a liquid electronic device, an electrochromic, a gas discharge display device and so forth may be used as the indicator 50. Needless to say, the indicator may be of an analog display type or a digital display type. The indicator 50 may also be disposed in the proximity of the hand piece 4. This arrangement is more convenient because the operator can always check the laser power.

It is extremely effective to dispose the laser power meter 20 on the control panel 61 as shown in the drawing. During the surgical operation, the operation of the hand piece must be frequently interrupted. If the laser light is emitted accidentally while the hand piece is left standing, it is dangerous to the people inside the surgical operation room. This danger can be prevented if the hand piece is fitted into the laser power meter 20.

In the surgical operation such as the neurosurgery, for example, the operation time sometimes lasts for more than six hours. In such a case, the laser power of the laser surgical equipment is likely to change depending upon the laser oscillator, deviation of the optical axis of the waveguide, fatigue of the lenses of the hand piece, and so forth. In order to measure the laser power from time to time during the surgical operation extending for a long period of time, therefore, the laser power meter 20 is preferably placed close to the operator. In such a case, the laser power meter 20 is of a detachable type so that it can be removed from the control panel 61.

Figure 8:
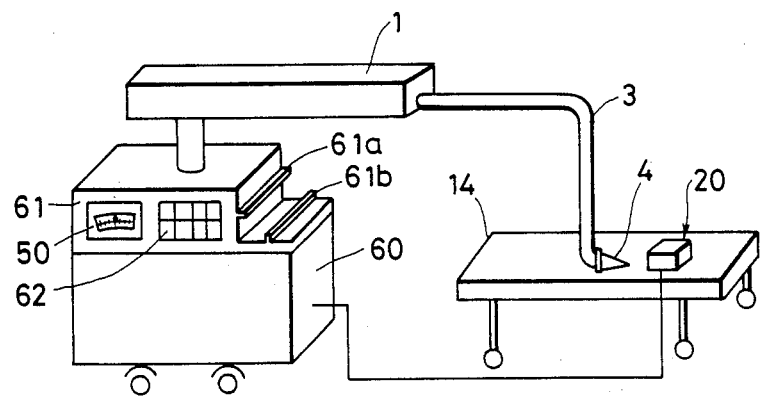
Figure 9:
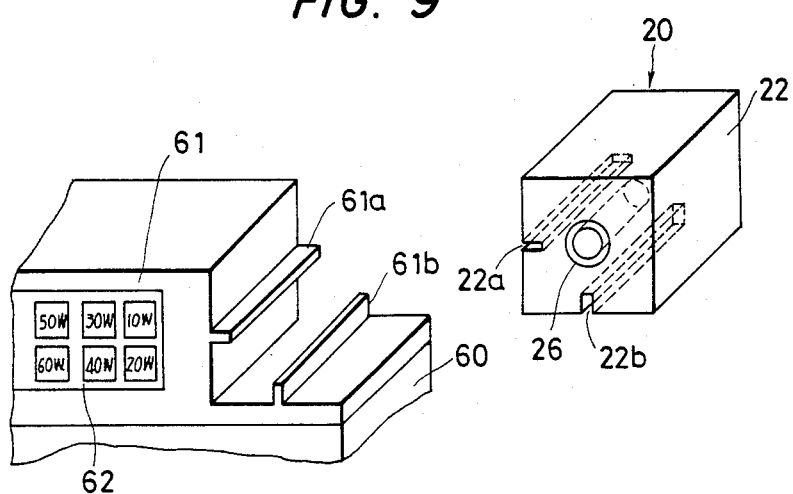
FIGS. 9 and 10 show another example of the laser power meter.

FIG. 9 shows an example of the laser power meter 20 of the detachable type. Grooves 22a and 22b are defined on the side and bottom of the case 22 of the laser power meter 20, respectively, while guide rails 61a and 61b to mate with these grooves are defined at a part of the control panel 61. Thus, the laser power meter can be fitted to the control panel 61 by fitting the guide rails 61a and 61b into the grooves 22a and 22b of the laser power meter 20. The laser power meter 20 can be independently used as the meter if it is removed from the control panel 61. If the laser power meter 20 is disposed in the proximity of the operating table with its output being applied to the comparison circuit 40 and the display 50 inside the control panel by a wire or wireless system as shown in FIG. 8, the operator can measure the laser power at hand and can carry out reliably the surgical operation by using alway the stable and accurate laser power even when the surgical operation continues for an extended period of time. Incidentally, the laser power meter 20 is preferably as compact as possible so as not to hinder the surgical operation. In the embodiment shown in FIG. 4, the case 22 is 100 mm wide, 100 mm high and 200 mm deep. Being sufficiently compact, it does not hinder the surgical operation even if placed close to the operating table.

Figure 10:
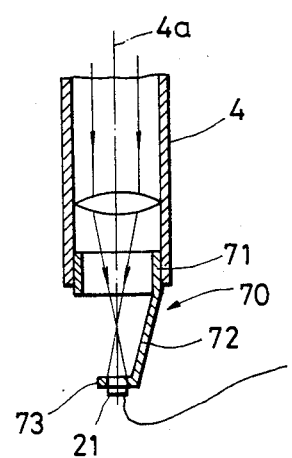

FIG. 10 shows another example of the laser power meter used in the present invention. This laser power meter eliminates the necessity of the case 22 of the laser power meter shown in FIG. 4 and reduces the size of the laser power meter and eventually, the size of the laser surgical equipment as a whole. In this embodiment, the photo-detector 21 explained with reference to FIG. 5 is fitted to the tip of the hand piece 4, whenever necessary. The photo-detector 21 is fitted by use of an attachment 70 such as shown in the drawing, for example. The attachment 70 consists of a cylindrical portion 71 which is detachable to and from the hand piece 4, a parallel-like leg 72 extending from one end of the cylindrical portion to the axis 4a of the hand piece 4 and a circular edge plate portion 73 formed substantially vertically at the tip of the leg 72. The cylindrical portion 71, the leg 72 and the edge plate portion 73 are formed in a unitary structure with one another. A T-shaped slot groove is formed on the cylindrical portion 71 so that the attachment can be quickly fitted to and removed from the hand piece 4. The leg 72 is formed in parallel with the axis 4a or is inclined inward and its length is decided so that the edge plate portion 72 is placed in the proximity of the focal point of the laser light from the hand piece. The photo-detector 21 is disposed in the opening at the center of the edge plate portion 73. When the attachment 70 is fitted to the hand piece 4, the photo-detector 21 receives the laser light emitted from the hand piece. The output of the photo-detector 21 is applied to the comparison circuit 40 and to the indicator 50 by the wire or wireless system in the same way as in the foregoing example. In this embodiment, the diameter of the photo-detector 21 is up to about 8 mm and the heat capacity is small because the size of the hand piece (diameter=approx. 20 mm, length=approx. 100 mm) is limited. To measure the high laser light of a 100 W output, therefore, time control is preferably made so as to oscillate the laser oscillator below about 1 second in order to prevent thermal damage of the photo-detector.

This embodiment makes it possible to accurately measure the laser power at the diseased part or at the tip of the hand piece and to automatically set the laser power required by the operator. The laser power meter has the function of holding the hand piece and eliminates the danger of erroneous or accidental emission of the laser light when the operator leaves the hand piece standing. Hence, a laser surgical equipment having high safety can be obtained.

Medical or surgical appliances and equipment such as the laser surgical equipment must always operate stably. Accordingly, the laser surgical equipment preferably has a self-diagnosing function which detects the trouble in any of the laser oscillator, the waveguide and the hand piece if the laser power at the tip of the hand piece drops, for example. Next, still another embodiment of the present invention which makes possible such self-diagnosis will be described.

Figure 11:
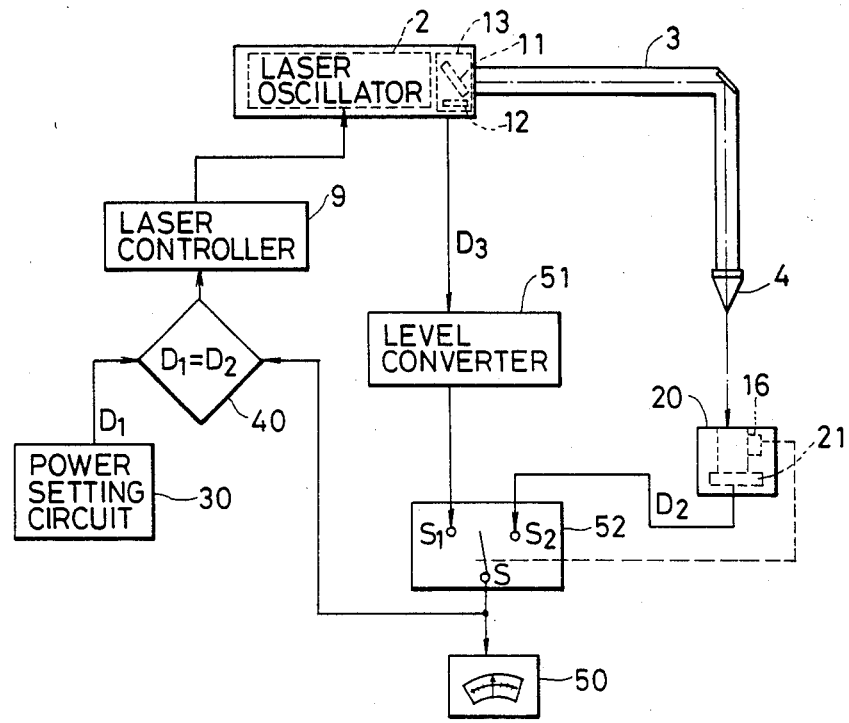
FIG. 11 is a block diagram of the laser surgical equipment in accordance with another embodiment of the present invention.

FIG. 11 is a block diagram of the laser surgical equipment making possible monitoring of the laser power during the surgical operation as well as the self-diagnosis of the equipment. First, monitoring of the laser power during the surgical operation is carried out in accordance with the following sequence:

(1) The laser power $D_h$ at the tip of the hand piece is measured by the laser power meter 20 immediately before the equipment is used for the surgical operation.

(2) The output $D_l$ of the laser oscillator in this case is measured by the laser power meter 13.

(3) A coefficient k which satisfies the relation $D_h = k \cdot D_l$ is obtained.

(4) The output $D_l$ of the laser oscillator is level-converted by the coefficient k and is displayed when the hand piece 4 is used for the surgical operation.

The laser power at the tip of the hand piece can be monitored on the real time basis during the surgical operation in accordance with the sequence described above.

Figure 12:
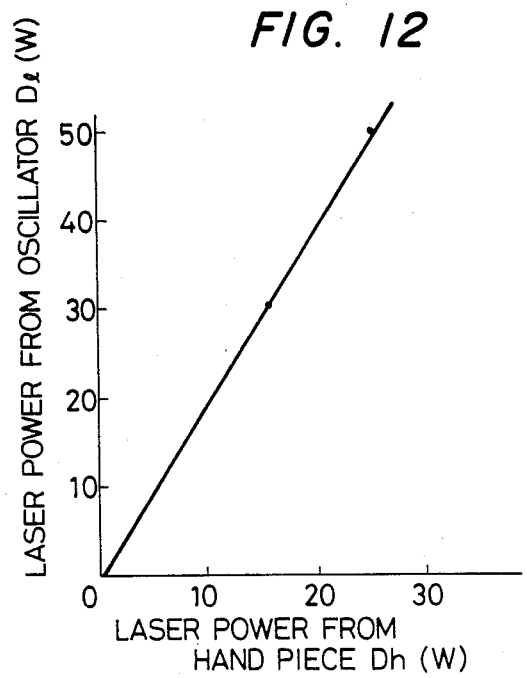
FIG. 12 is a diagram showing the relation between the hand piece output and the output of the laser oscillator.

FIG. 12 shows the relation between $D_h$ and $D_l$ as a result of experiments carried out by the inventors of the present invention. The correction coefficient k of about 0.54 can be obtained from this relation. The value of the correction coefficient k remains unchanged within the range of the output $D_l$ of the laser oscillator of from 0 to 50 W.

It is preferred to first adjust the power $D_h$ at the tip of the hand piece by the automatic laser power adjuster described above and then to determine the correction coefficient k in accordance with the present invention. For, if the power is set to 20 W by the laser power setting circuit 30, $D_h = 20$ W can be automatically obtained by the comparison circuit 40. The accurate correction coefficient k can be obtained simply by measuring $D_l$ in this case by the laser power meter 13. For monitoring purposes during the surgical operation, the laser surgical equipment of this embodiment includes the proximity switch 16 disposed in the laser power meter 20, a level converter 51 which is connected to the photo-detector 12 of the laser power meter 13 and converts the level of the output $D_3$ of the photo-converter and a change-over switch 52 which changes over the output of the level converter 51 and the output of the photo-converter 21 of the laser power meter 20 and applies it to the indicator 50. During the surgical operation, the change-over switch 52 selects the terminal S1 and applies the output of the level converter 51 to the indicator 50.

When the hand piece 4 is fitted into the laser power meter 20, the change-over switch 52 selects the terminal $S_2$ in the interlocking arrangement with the operation of the proximity switch 16 of the laser power meter 20 and applies the output of the photo-converter 21 to the indicator 50. The hand piece 4 is first inserted into the laser power meter 20 and the power $D_h$ at the tip of the hand piece is adjusted to a desired value by the laser power setting circuit 30, the comparison circuit 40 and the laser power controller 9. The output $D_2$ of the photo-converter in this case is applied to the indicator 50 and is displayed by the indicator. (The output $D_2$ corresponds to the power $D_h$ at the tip of the hand piece.) Next, when the hand piece 4 is removed from the laser power meter 20, the switch 52 selects the terminal $S_1$ and applies the output $D_3$ of the photo-detector 12 to the indicator 50 via the level converter 51 so as to display the output $D_3$ (corresponding to the output $D_l$ of the laser oscillator). The level converter 51 is then adjusted so that the output $D_3$ of the photo-detector 12 coincides with the output of the photo-detector 21 and is displayed on the indicator 50. Thus, the measured value displayed on the indicator during the surgical operation becomes equal to the laser power at the tip of the hand piece. Furthermore, the output of the level converter 51 is applied to the comparison circuit 40 and the laser power is kept constant during the surgical operation by the output of the level converter 51.

As described above, the energy of the laser light at the diseased part can be measured by the laser power meter 20, the level converter 51 and the change-over switch 52 even during the surgical operation.

This embodiment uses the beam splitter 11 in combination with the photo-detector 12 as the laser power meter 13 for detecting the output $D_l$ of the laser oscillator but it is also possible to dispose the photo-detector at the rear of the total reflector of the laser oscillator so as to detect the laser light leaking from the total reflector. In this case, the beam splitter becomes unnecessary.

Figure 13:
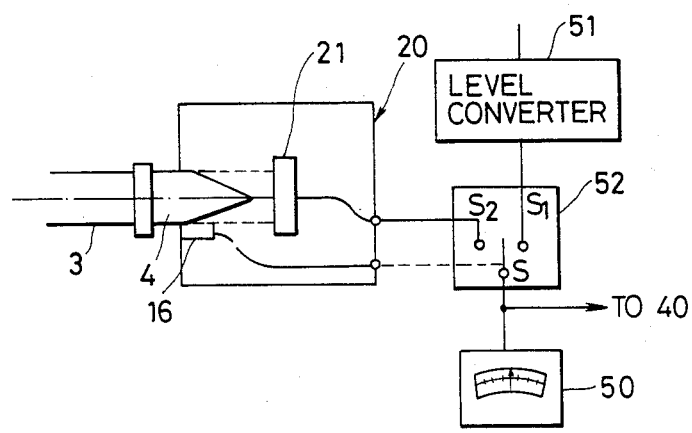
FIG. 13 is a block diagram showing still another example of laser power meter.

Next, one embodiment of the laser power meter 20 used in the equipment of the present invention is shown in FIG. 13. The drawing illustrates the state in which the hand piece 4 is inserted into the laser power meter 20. When the laser light is radiated through the waveguide 3 and the hand piece 4 under this state, the energy of the laser light is detected by the photo-detector 21, whose output is applied to the comparison circuit 40 and to the indicator 50 via the switch 52. The proximity switch 16 detects that the hand piece 4 is inserted into the laser power meter 20. Upon coming into contact with the hand piece, the proximity switch 16 actuates the switch 52, makes it select the terminal $S_2$ and applies the output of the photo-detector 21 to the indicator 50. The proximity switch may be of such a type that detects the change in the electrostatic capacitance occurring when the relay switch comes into contact with the hand piece, for example. The switch 52 can be realized by an analog switch.

Figure 14:
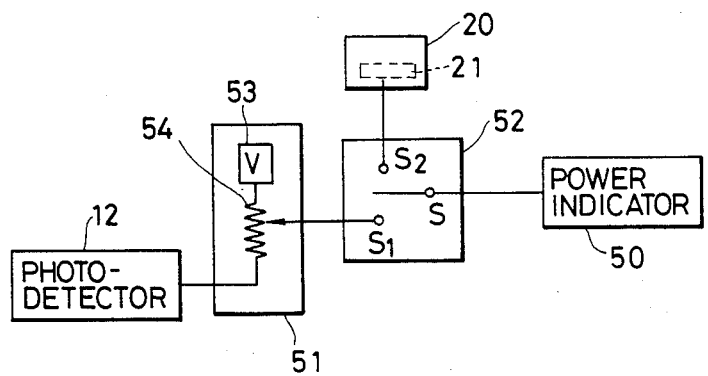
FIG. 14 is a block diagram showing an example of level converter to be used in the present invention.

Next, an example of the level converter 51 will be described with reference to FIG. 14. The level converter 51 consists of a variable resistor 54 whose one end is connected to the photo-detector 12 and a d.c. voltage source 53 which is connected to the other end of the variable resistor 54. The variable resistor 54 adjusts the division ratio between the output of the photo-detector 12 and the voltage V of the power source 53 so that the output of the photo-detector 12 can be brought into conformity with the output of the photo-detector 21 of the laser power meter 20 and be displayed on the indicator 50.

Figure 15:
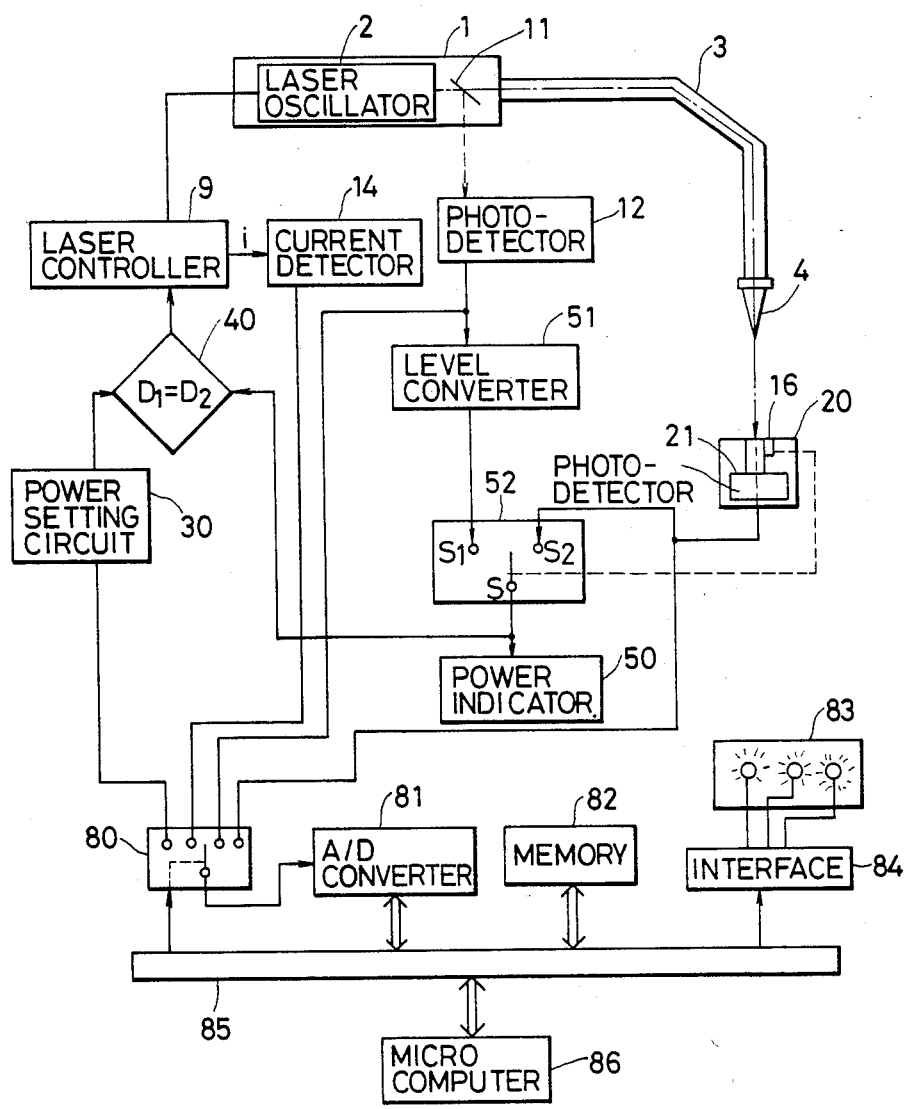
FIG. 15 is a block diagram showing the laser surgical equipment in accordance with still another embodiment of the present invention.

The laser surgical equipment in accordance with the present invention has the self-diagnosing function. The laser oscillation current i from the laser controller 9 and the laser power of the laser oscillator 2 are primarily determined when the laser oscillator operates normally. When the laser power from the hand piece 4 is automatically adjusted by use of the output of the photo-detector 21, for example, the abnormality of the laser oscillator 2 can be detected if the oscillation current i flows in excess. The abnormality of the optical system of the waveguide 3 or that of the hand piece 4 can be detected if the correction coefficient k is abnormally small when the outputs of the photo-detectors 12 and 21 are compared with each other. An example of the circuit construction for the self-diagnosis of the laser surgical equipment is shown in FIG. 15. The drawing shows the case in which self-diagnosis is effected by a micro-computer 86. Four input data are necessary for the self-diagnosis of the laser surgical equipment, i.e., the laser power set value, the oscillation current i of the laser oscillator, the laser power of the laser oscillator and the laser power at the tip of the hand piece. They may be the output of the laser power setting circuit 30, the output of the current detector 14 connected to the laser oscillation controller 9, the output of the photo-detector 12 and the output of the photo-detector 21, respectively. These four kinds of currents or voltages are applied to a multiplexer 80. The micro-computer 86 sequentially changes over the four inputs of the multiplexer 80 and sends the data to the A/D converter 81. The digital data converted by the A/D converter 81 are transferred to a memory 82 through a common bus line 85. The microcomputer 86 analyzes the content of the memory 82 storing therein the laser power set value, the laser oscillation current, the laser power of the laser oscillator and the laser power at the tip of the hand piece and diagnoses the trouble of the equipment. The result lights warning lamps of the warming indicator 83 through an interface 84. The warning lamps are arranged so as to light the lamps corresponding to the trouble of the laser oscillator, the waveguide and the hand piece, respectively.

The self-diagnostic algorithm of the equipment will be now explained. The trouble of the laser oscillator, if any, can be diagnosed from the following phenomena:

(1) when the output of the laser oscillator detected by the photo-detector 12 does not reach the set value; and (2) when the oscillation current of the oscillator 2 is abnormally great.

Figure 16:
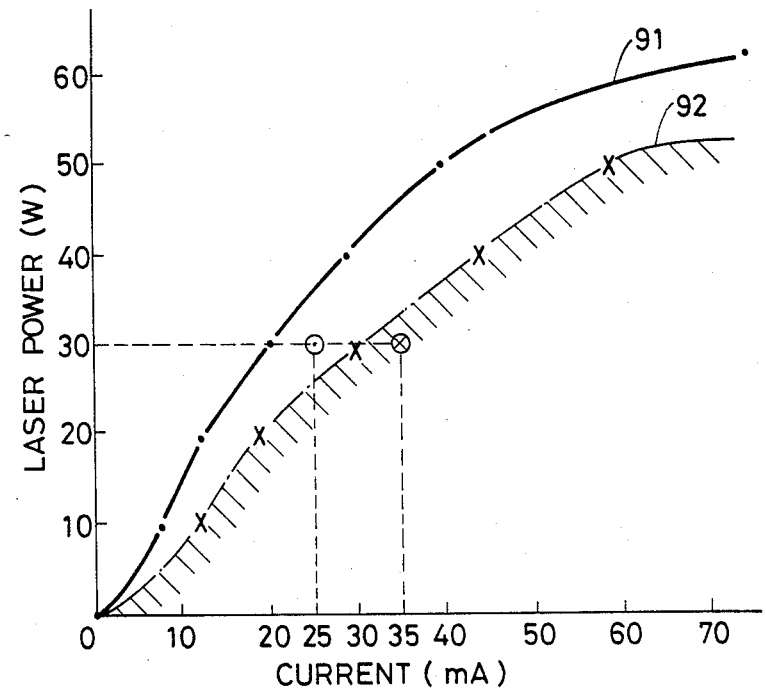
FIG. 16 is a diagram showing the relation between the oscillation current of the laser oscillator and the laser power.

In the first case, the surgical operation by the laser surgical equipment is not possible and the equipment must be immediately repaired or adjusted. In the second case, the equipment can be used for the surgical operation but must be inspected and adjusted after the surgical operation. The solid line 91 in FIG. 16 shows the relation between the oscillation current and the laser power of the laser oscillator obtained by the experiments conducted by the inventors of the present invention. If the oscillation efficiency drops due to degradation of the laser oscillator, for example, the oscillation current must be increased in order to obtain the same laser power. If the increment 50% of the oscillation current is a limit value as represented by the dotted line 92 in FIG. 16, the range below the dotted line represents an abnormal current. If the output of the laser oscillator is 30 W in FIG. 16, for example, the oscillation current of 25 mA is "normal" while the oscillation current of 35 mA is "abnormal". Thus, the abnormality and normality of the laser oscillator can be detected by monitoring the laser output and oscillation current of the laser oscillator to be applied to the computer.

Furthermore, the trouble of the waveguide and hand piece of the laser surgical equipment can be diagnosed from the following penomena:

(1) when the output of the waveguide 3 (the output of the photo-detector 21 when the hand piece 4 is not fitted to the waveguide 3 but the waveguide 3 is inserted into the laser power meter 20) is abnormally smaller in comparison with the output of the laser oscillator 2 (the output of the photo-detector 12); and (2) the power at the tip of the hand piece when the hand piece 4 is fitted to the waveguide 3 (the output of the photo-detector 21 when the hand piece 4 is inserted into the laser power meter 20) is abnormally smaller in comparison with the output of the laser oscillator (the output of the photo-detector 12).

Figure 17:
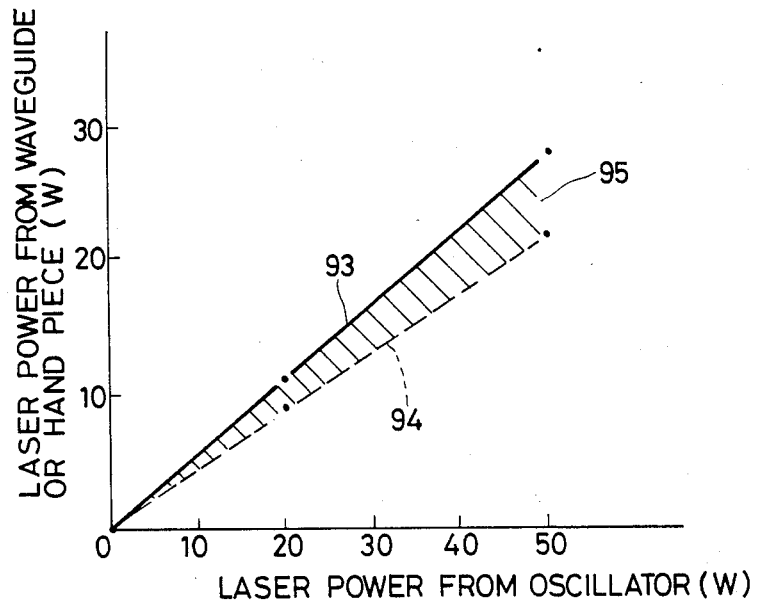
FIG. 17 is a diagram showing the relation between the laser power from the waveguide or hand piece and the laser power from the laser oscillator.

FIG. 17 shows the relation between the laser power in the waveguide and at the tip of the hand piece and the output of the laser oscillator, the results being obtained by the experiments conducted by the inventors of the present invention. As can be seen from the diagram, the output of the waveguide (represented by the solid line 93) is about 60% with respect to the oscillator output and the loss of the waveguide is about 40%. According to the calculation, the loss due to the reflectivity is about 15% when the waveguide 3 is composed of a 7-joint 8-mirror multiple-joint mirror system. It can be thus assumed that among the 40% loss of the waveguide shown in FIG. 17, 15% loss results from the reflection loss by the multi-joint mirror while 25% loss results from the deviation of the optical axis. Hence, the optical axis of the waveguide must be re-adjusted. Accordingly, the equipment can be diagnosed as being "abnormal" if the output of the waveguide is below 75% of the output of the laser oscillator and the optical axis of the waveguide must be adjusted in such a case.

In FIG. 17, the dotted line 94 represents the power at the tip of the hand piece. It can be seen from the diagram that the loss of the hand piece is about 20% (the oblique line portion 95 interposed between the solid line 93 and the dotted line 94 in the diagram). The hand piece is equipped with a lens for contracting the laser light which is substantially parallel and the reflection absorption by this lens is up to about 2% if a reflection preventing film is applied to the lens. Accordingly, the loss of the hand piece described above substantially arises from the contamination of the lens or the like. From this, the equipment can be diagnozed as being "abnormal" if the laser power at the tip of the hand piece is below 90% of the output of the waveguide, and the contamination of the lens or the like may be removed in such a case.

As described above, the troubles of the laser oscillator, the waveguide and the hand piece can be diagnosed by monitoring the oscillation current and laser output of the laser oscillator, the laser output of the waveguide and the laser output at the tip of the hand piece.

Figure 18:
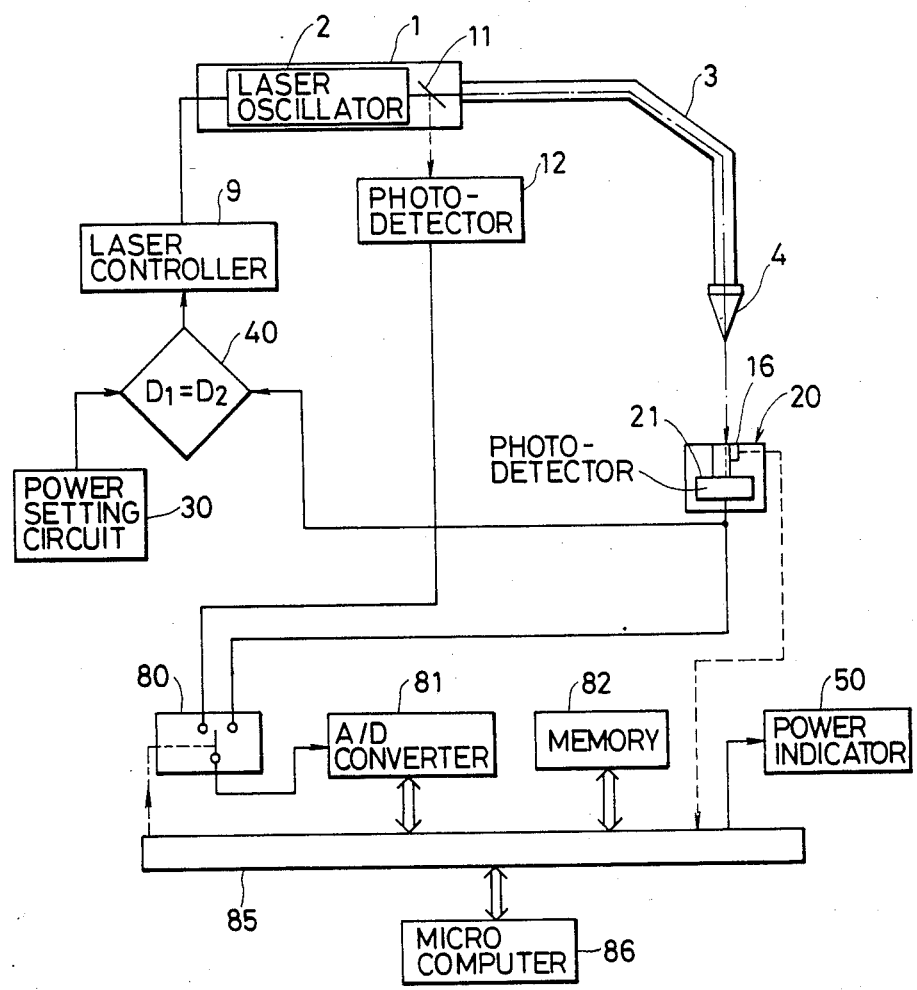
FIG. 18 is a block diagram of the laser surgical equipment in accordance with still another embodiment of the present invention.

Monitoring can be effected on the real time basis shown in FIG. 11 by use of the micro-computer system shown in FIG. 15. FIG. 18 shows an embodiment in which the micro-computer is applied on the real time basis.

The outputs of the photo-detectors 12 and 21 are applied to the multiplexer 80, whose switch is connected via the common bus line 85 so as to operate in the interlocking arrangement with the operation of the proximity relay 16. The outputs $D_3$ and $D_2$ of the photo-detectors 12 and 21 are stored in the memory 82 via the A/D converter 82. The micro-computer 86 calculates the coefficient k which satisfies the relation $D_2 = k \cdot D_3$. After the output $D_3$ of the photoconvertor 12 is multiplied by the coefficient k, it is level-converted to the output $D_2$ l *of the photodetector* 21 *and is applied to the indicator* 50. *Accordingly, the laser power equivalent to the laser power at the tip of the hand piece can be displayed on the indicator during the surgical operation.*

As described in the foregoing, the present invention makes it possible to always measure the laser energy at the diseased part during the surgical operation and hence, the operator can operate with the accurate laser power. The laser surgical equipment of the present invention has the self-diagnostic function to detect the trouble and provides a surgical equipment which always operates stably.

What is claimed is:

1. A laser surgical equipment comprising:
a laser oscillator for oscillating a laser output;
control means for controlling the laser output of said laser oscillator;
an optical waveguide connected to said laser oscillator and transmitting the laser output;
a hand piece connected to said optical waveguide and radiating the laser output to a diseased part to be radiated;
first detection means for detecting the laser output from said hand piece;
setting means for setting a desired laser output from said hand piece;
comparison means for comparing the output of said first detection means with an output of said setting means and for controlling said control means; and
memory means for storing the output of said comparison means, said memory means providing an output to said control means controlling the laser output of said laser oscillator during the period other than the period in which said first detection means detects the laser output.

2. The laser surgical equipment as defined in claim 1, wherein said first detection means consist of a case having a holding member for holding said hand piece while said hand piece is fitted to one end of said holding member, and a photoelectric conversion element disposed so as to receive the laser light while said hand piece is inserted into said holding member inside said case.

3. The laser surgical equipment as defined in claim 3 wherein means for detecting the insertion of said hand piece are disposed on said holding member, and the output of said insertion detecting means is used for detecting the period in which said first detection means detect the laser output.

4. The laser surgical equipment as defined in claim 2 or 3, wherein said case is disposed on a control panel.

5. The laser surgical equipment as defined in claim 4, wherein said case is disposed detachably.

6. The laser surgical equipment as defined in claim 1 wherein said first detection means consist of a photoelectric conversion element disposed detachably on said hand piece.

7. The laser surgical equipment as defined in claim 1 which further includes second detection means for detecting the laser output of said laser oscillator and display means for displaying the output of said second detection means.

8. The laser surgical equipment as defined in claim 1, wherein said control means is responsive to the output of said comparison means for automatically controlling the laser output of said laser oscillator in accordance therewith.

9. The laser surgical equipment as defined in claim 1, wherein said control means is responsive to said comparison means for automatically controlling the laser output of said laser oscillator so that the output of said first detection measn becomes equal to the output of said setting means.

10. A laser surgical equipment comprising:
a laser oscillator for oscillating a laser output;
control means for controlling the laser output of said oscillator;
an optical waveguide connected to said laser oscillator and transmitting the laser output;
a hand piece connected to said optical waveguide and radiating the laser output to a diseased part to be radiated;
first detection means for detecting the laser output from said hand piece;
setting means for setting a desired laser output from said hand piece;
comparison means for comparing the output of said first detection means with an output of said setting means and for controlling said control means;
second detection means for detecting the laser output of said laser oscillator;
level conversion means connected to said second detection means for converting the output of said second detection means into an output corresponding to the output of said first detection means; and
display means for displaying the output of said level conversion means.

11. The laser surgical equipment as defined in claim 10, which further includes change-over means for receiving the output of said first detection means and the output of said conversion means and applying either of the outputs to said comparison means and to said display means.

12. The laser surgical equipment as defined in claim 11, which further includes means for detecting the period in which said first detection means detect the laser output and the output of said period detecting means is used for controlling said change-over means.

13. The laser surgical equipment comprising:
a laser oscillator for oscillating a laser output;
control means for controlling the laser output of said laser oscillator;
an optical waveguide connected to said laser oscillator and transmitting the laser output;
a hand piece connected to said optical waveguide and radiating the laser output to a diseased part to be radiated;
first detection means for detecting the laser output from said hand piece;
setting means for setting a desired laser output from said hand piece;
comparison means for comparing the output of said first detection means with an output of said setting means and for controlling said control means so that the output of said first detection means becomes equal to the output of said setting means;
second detection means for detecting the laser output of said laser oscillator:
display means for displaying the output of said second detection means:
third detection means for detecting an oscillation current of said laser oscillator;
memory means for storing the outputs of said first detection means, said second detection and said third detection means; and
determination means for determining whether or not said laser surgical equipment operates normally, by analyzing the content of said memory means.

14. The laser surgical equipment as defined in claim 13, wherein said determination means are means for determining the normality and abnormality of said laser oscillator from the relation between the output of said third detection means and the output of said second detection means.

15. The laser surgical equipment as defined in claim 13 wherein said determination means are means for determining the normality and abnormality of said optical waveguide or said hand piece from the relation between the output of said first detection means and the output of said second detection means.

* * * * *